(12) United States Patent
Gregorich et al.

(10) Patent No.: US 8,956,403 B2
(45) Date of Patent: Feb. 17, 2015

(54) MEDICAL IMPLANT INCLUDING A MAGNESIUM-BASED TIE LAYER

(75) Inventors: Daniel J. Gregorich, Plymouth, MN (US); Michael P. Meyer, Richfield, MN (US); Jonathan S. Stinson, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 13/238,234

(22) Filed: Sep. 21, 2011

(65) Prior Publication Data
US 2012/0095548 A1 Apr. 19, 2012

Related U.S. Application Data

(60) Provisional application No. 61/394,133, filed on Oct. 18, 2010.

(51) Int. Cl.
| | | |
|---|---|---|
| A61F 2/02 | (2006.01) |
| A61L 31/02 | (2006.01) |
| A61L 27/04 | (2006.01) |
| A61L 27/30 | (2006.01) |
| A61L 27/54 | (2006.01) |
| A61L 31/08 | (2006.01) |
| A61L 31/16 | (2006.01) |

(52) U.S. Cl.
CPC ............... *A61L 31/022* (2013.01); *A61L 27/04* (2013.01); *A61L 27/306* (2013.01); *A61L 27/54* (2013.01); *A61L 31/088* (2013.01); *A61L 31/16* (2013.01); *A61L 2300/00* (2013.01)
USPC ......................... 623/1.42; 623/1.44; 623/1.46

(58) Field of Classification Search
USPC ...................... 623/1.45, 1.15, 1.42, 1.44, 1.46
See application file for complete search history.

(56) References Cited

U.S. PATENT DOCUMENTS

| 6,290,721 | B1 | 9/2001 | Heath | |
|---|---|---|---|---|
| 7,641,983 | B2 * | 1/2010 | Stinson | 428/546 |
| 2007/0135908 | A1 * | 6/2007 | Zhao | 623/1.46 |
| 2008/0051881 | A1 * | 2/2008 | Feng et al. | 623/1.39 |
| 2008/0160259 | A1 * | 7/2008 | Nielson et al. | 428/148 |

(Continued)

FOREIGN PATENT DOCUMENTS

WO WO2010118193 A2 10/2010

OTHER PUBLICATIONS

International Search Report and Written Opinion; Feb. 28, 2012; World Intellectual Property Organization (WIPO) (International Bureau Of); PCT/US2011/052486; 11 pages.

(Continued)

*Primary Examiner* — Randy Shay
*Assistant Examiner* — Dinah Baria
(74) *Attorney, Agent, or Firm* — Fish & Richardson P.C.

(57) ABSTRACT

A medical implant includes a metallic base, a tie layer, and at least a first layer overlying an outer surface of the tie layer. The tie layer is bonded to at least a portion of a surface of the metallic base. The tie layer includes magnesium or a magnesium-based alloy. The tie layer can have an outer surface comprising dendritic grains. The tie layer can have a rough outer surface defined by pores, projecting grain structures, and/or projecting particles. A method of producing a tie layer on a medical device includes applying magnesium or a magnesium-based alloy to the medical device and cooling the magnesium or the magnesium-based alloy to produce a rough outer surface.

19 Claims, 3 Drawing Sheets

(56) References Cited

U.S. PATENT DOCUMENTS

| | | | |
|---|---|---|---|
| 2008/0177378 A1* | 7/2008 | Asgari | 623/1.38 |
| 2008/0208313 A1 | 8/2008 | Yu et al. | |
| 2009/0088834 A1* | 4/2009 | Wang | 623/1.15 |
| 2009/0118814 A1* | 5/2009 | Schoenle et al. | 623/1.15 |
| 2009/0157165 A1* | 6/2009 | Miller et al. | 623/1.15 |
| 2009/0196899 A1* | 8/2009 | Birdsall et al. | 424/423 |
| 2010/0057197 A1 | 3/2010 | Weber et al. | |
| 2010/0262222 A1* | 10/2010 | Weber | 623/1.15 |

OTHER PUBLICATIONS

International Preliminary Report on Patentability issued on May 2, 2013 by The WIPO in the international application No. PCT/US2011/052486, 8 pages.

Erinc et al., "Applicability of existing magnesium alloys as biomedical implant materials," *Magnesium Technology*, 2009, 209-214.

* cited by examiner

MEDICAL IMPLANT INCLUDING A MAGNESIUM-BASED TIE LAYER

CROSS-REFERENCE TO RELATED APPLICATIONS

This application claims priority under 35 U.S.C. §119(e)(1), to U.S. Provisional Application Ser. No. 61/394,133, filed on Oct. 18, 2010, the entire contents of which is incorporated herein.

TECHNICAL FIELD

This disclosure relates to medical implants having a tie layer including magnesium or a magnesium-based alloy.

BACKGROUND

A medical implant can replace, support, or act as a missing biological structure. Examples of medical implants include orthopedic implants, bioscaffolding, and endoprostheses such as stents, covered stents, stent-grafts, bone screws, and aneurysm coils. A medical implant can also add a new function to the body. For example, medical implants can include identification tags, communication devices, and/or pacemaking electrodes.

Endoprostheses can be implanted in various body passageways such as arteries, other blood vessels, and other body lumens (e.g., neural pathways). These passageways sometimes become occluded or weakened. For example, the passageways can be occluded by a tumor, restricted by plaque, or weakened by an aneurysm. When this occurs, the passageway can be reopened or reinforced, or even replaced, with an endoprosthesis. An endoprosthesis is typically a tubular member placed in a lumen in the body.

Endoprostheses can be delivered inside the body by a catheter. The catheter supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated and the catheter withdrawn.

In another delivery technique, the endoprosthesis is formed from an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

Endoprostheses can sometimes carry a drug, such as an antiproliferative, to reduce the likelihood of restenosis, i.e., reclosure of the vessel due to immune reactions by the body at the treatment site. For example, a drug-eluting layer can be coated onto an endoprosthesis.

SUMMARY

A medical implant having a metallic base, a tie layer, and at least a first layer overlying the tie layer is described herein. The tie layer is bonded to at least a portion of a surface of the metallic base. The tie layer includes magnesium or a magnesium-based alloy. The tie layer has an outer surface including dendritic grains. The first layer overlies the outer surface of the tie layer.

The metallic base can include a biostable metal. For example, the metallic base can include a metal selected from the group consisting of stainless-steels, platinum-enhanced stainless steels, cobalt-chromium alloys, nickel-titanium alloys, niobium-based alloys, titanium-based alloys, and tantalum-based alloys. In other embodiments, the metallic base can include a bioerodible metal (e.g., iron or a bioerodible iron alloy). The metallic base, in some embodiments, includes a metal having a melting temperature greater than the melting temperature of the magnesium or the magnesium-based alloy of the tie layer. For example, the metallic base can include a metal having a melting temperature of 700° C. or greater.

The dendritic grains, in some embodiments, have a maximum dimension of between 10 microns and 50 microns. The dendritic grains can protrude from the tie layer, providing a rough outer surface.

In some embodiments, the tie layer includes pure magnesium. In other embodiments, the tie layer includes a magnesium-based alloy. The magnesium-based alloy can include zinc, aluminum, calcium, tin, rare earth metals, or a combination thereof.

The tie layer can further include particles within a matrix of the magnesium or the magnesium-based alloy. The particles can partially protrude from the surface of the tie layer, in order to provide a rough outer surface. The particles can have a maximum dimension of between 10 microns and 50 microns. The particles can be iron particles, calcium powder, graphite spheres, graphite nanotubes, barium powder, or a combination thereof. In some embodiments, the particles are bioerodible.

The tie layer, in some embodiments, has an average thickness of between 1 micrometer and 20 micrometers.

The first layer can include one or more therapeutic agents. In some embodiments, the first layer can include a polymer. For example, the first layer can be a drug-eluting first layer. In some embodiments, the first layer can include a ceramic (e.g., iridium oxide, titanium oxide, or aluminum oxide). In some embodiments, the medical implant can include a plurality of layers overlying the tie layer.

The medical implant can be a stent. For example, the metallic base can include a plurality of bands and a plurality of connectors extending between adjacent bands and the surface of the metallic base can be at least a portion of an abluminal surface of the bands and connectors.

In another aspect, a medical implant having a metallic base, a tie layer having a rough outer surface, and at least a first layer overlying the rough outer surface of the tie layer is described herein. The tie layer includes magnesium or a magnesium-based alloy. The rough outer surface is defined by pores, projecting grain structures, projecting particles at least partially embedded in the magnesium or the magnesium-based alloy, or a combination thereof. The tie layer has an average thickness of between 1 micrometer and 20 micrometers.

In another aspect, a method of forming a tie layer on a medical implant is described. The method includes applying magnesium or a magnesium-based alloy to at least a portion of a surface of a medical implant and cooling the magnesium or the magnesium-based alloy to produce a tie layer having a rough outer surface. The medical implant includes a metallic composition having a melting temperature greater than melting temperature of the magnesium or the magnesium-based alloy. The magnesium or magnesium-based alloy is applied at a temperature between the melting temperature of the metallic composition of the stent and the melting temperature of the magnesium or the magnesium-based alloy. Applying the magnesium or the magnesium-based alloy at a temperature lower than the melting temperature of the metallic base can permit limited diffusion bonding of the magnesium or the magnesium-based alloy to the metallic base.

In some embodiments, the magnesium or the magnesium-based alloy is cooled at a rate sufficient for producing a microstructure comprising dendritic grains. Dendritic grains form as the magnesium or magnesium-based alloy solidifies on the substrate. Relatively fast cooling that would occur in a thin Mg coating on a relatively thick substrate would produce fine dendrite crystallites. Slower cooling would produce a coarser dendritic grain structure. Coarse dendritic grains can protrude from the tie layer to provide the rough outer surface similar to "orange peel" structure on coarse grain or galvanized steel. In some embodiments, a magnesium-based alloy is applied such that it includes multiple phases. The magnesium-based alloy can be etched after solidification to remove certain phases to leave a plurality of grain structures projecting from the surface of the tie layer. In some embodiments, the magnesium-based alloy can be formed in-situ by first applying a layer of magnesium, followed by applying a second metal. The magnesium and the second metal can then be alloyed by heating the layered structure to a temperature between the melting temperature of the magnesium and the melting temperature of the metallic base.

In other embodiments, the magnesium or the magnesium-based alloy is cooled at a rate sufficient to create shrinkage-induced porosity in the magnesium or the magnesium-based alloy. Shrinkage porosity is formed when the Mg solidifies at a rapid rate such that there is not enough bulk liquid metal in the coating to backfill voids that fill as liquid metal transforms to solid metal with a contraction in volume. This can be accomplished by directing a gas nozzle upon the coating just as it exits from the coating bath. Inert gas, such as argon, can be jetted through a nozzle to cause rapid cooling of the liquid Mg metal laying on the substrate. The gas impingement may also entrap gas molecules in the solidifying metal creating gas porosity in addition to shrinkage porosity. Furthermore, the gas impingement may create turbulence and waves in the liquid metal coating the substrate surface that upon solidification would result in surface contortions that contribute to overall roughness.

In some embodiments, particles are combined with the magnesium or the magnesium-based alloy to produce a matrix of the magnesium or the magnesium-based alloy having particles protruding therefrom to provide the rough outer surface. The particles can have a maximum dimension of between 10 microns and 50 microns.

Various embodiments of the subject matter described herein may provide one or more of the following advantages. In one or more embodiments, a magnesium or magnesium-based alloy containing a tie layer may result in a more secure and robust attachment of a therapeutic layer to a metallic stent. For example, the tie layer may inhibit detachment of large portions of a bioerodible therapeutic layer as it erodes. In some embodiments, a magnesium or magnesium-based alloy tie layer may bioerode to leave behind a bare metal stent. In one or more embodiments, the magnesium or magnesium-based alloy tie layer can be deposited at a temperature below the melting temperature of the metallic stent, which may reduce changes in the material properties of the metallic stent. Moreover, the tie layer may erode, leaving a stable and biocompatible metallic base surface, which can limit unwanted biological reactions.

The details of one or more embodiments are set forth in the accompanying drawings and the description below. Other features, objects, and advantages will be apparent from the description and drawings, and also from the claims.

DESCRIPTION OF DRAWINGS

Like reference symbols in the various drawings indicate like elements.

DETAILED DESCRIPTION

Figure 1:
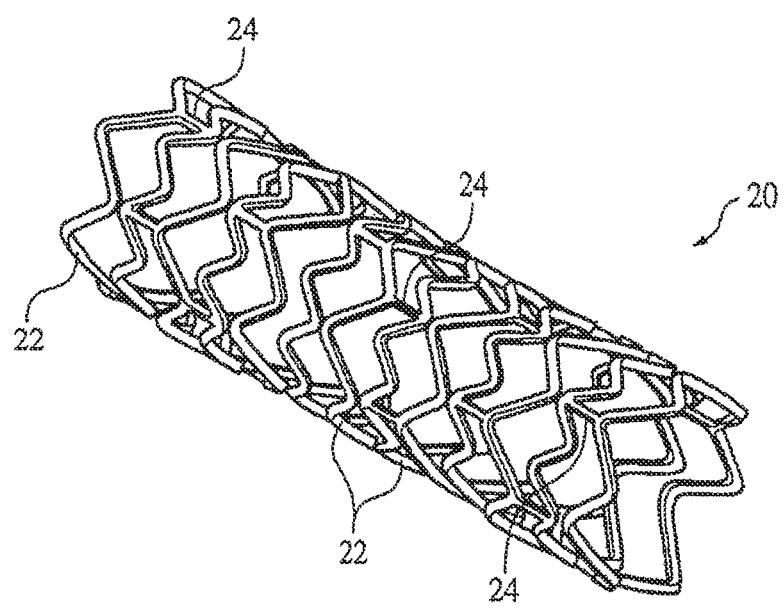
FIG. 1 illustrates an exemplary stent.

A stent 20, shown in FIG. 1, is discussed below as an example of one medical implant according to the instant disclosure. Stent 20 includes a pattern of interconnected struts forming a structure that contacts a body lumen wall to maintain the patency of the body lumen. For example, stent 20 can have the form of a tubular member defined by a plurality of bands 22 and a plurality of connectors 24 extending between and connecting adjacent bands. During use, bands 22 can be expanded from an initial, small diameter to a larger diameter to contact stent 20 against a wall of a vessel, thereby maintaining the patency of the vessel. Connectors 24 can provide stent 20 with flexibility and conformability, permitting the stent to adapt to the contours of the vessel. Other examples of endoprostheses can include covered stents and stent-grafts.

Figures 2A, 2B:
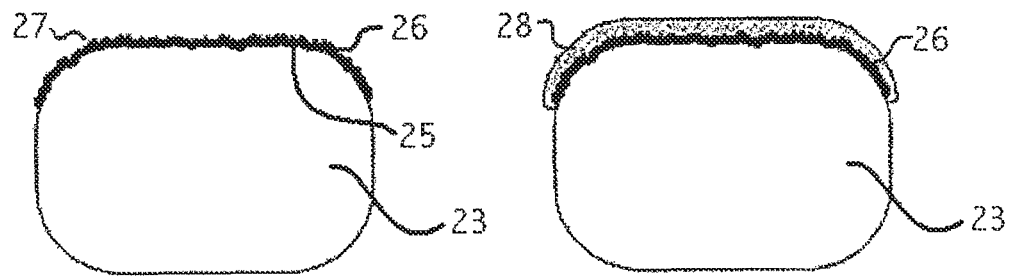
FIGS. 2A and 2B illustrate exemplary cross-sections of struts of stents.

As shown in FIG. 2A, one or more struts of stent 20 include a metallic base 23 and a tie layer 26. FIG. 2B shows a strut including a metallic base 23, a tie layer 26, and a first layer 28 overlying the tie layer. As shown, the tie layer 26 and the first layer 28 can be deposited on one side of the strut. In some embodiments, the stent 20 includes the tie layer 26 on only an abluminal surface of the stent 20. In other embodiments, the stent 20 can include the tie layer 26 on a luminal surface of the stent 20. In some embodiments, the stent 20 can include the tie layer 26 on side surfaces of each strut. The stent 20 can also be coated on all sides with tie layer 26.

The metallic base 23 can form the majority of the stent 20 and may provide the mechanical strength needed to maintain the patency of a lumen upon expansion of stent 20 to expand the lumen during an implantation of the stent 20. The metallic base 23 can have a variety of dimensions depending upon the particular material used and the intended application for the stent. In some embodiments, the metallic base includes a biostable metal. In some embodiments, the biostable metal can be stainless-steel, platinum-enhanced stainless steel, a cobalt-chromium alloy, a nickel-titanium alloy, a niobium-based alloy, a titanium-based alloy, a tantalum-based alloy, a platinum-based alloy, or some combination thereof. In other embodiments, the metallic base 23 can be a bioerodible metal (e.g., iron or a bioerodible iron alloy). In some embodiments, the metallic base consists essentially of a single metal or single metal alloy. In other embodiments, the metallic base 23 can include multiple metal parts. For example, multiple layers of different metals can be present. In some embodiments, an inner core or outer layer of a radiopaque metal (e.g., gold or platinum) can be present in or over another metal (e.g., stainless steel or Nitinol).

Magnesium is not very solubility in the stent materials discussed above. Interdiffusion, however, will occur regardless of solubility, because atoms from each mating material are free to exchange at elevated temperatures. Elemental concentration gradients can occur within the coating and substrate and across the interface between the two. The zone where there is alloying with limited solubility can be very thin (i.e., less than 1 micron). A zone of limited solubility can have a limited ductility due to the formation of intermetallics. Accordingly, a very thin layer of limited solubility can minimize strains due to the crimping and expansion in a stent, which are distributed throughout the concentration gradients, and thus minimize the risk of failure.

In some embodiments, at least the outer surface of the metallic base 23 has a melting temperature of greater than 650° C. In some embodiments, the metal or metal alloy along the outer surface of the metallic base 23 has a melting temperature of at least 700° C. In still other embodiments, the metal or metal alloy has a melting temperature of at least 800° C. For example, some stainless steels have a melting temperature of about 900° C. By using a metallic base metal or metal alloy having a melting temperature greater than the melting temperature of the tie layer, the tie layer may be bonded to the metallic base 23 with limited diffusion of the tie layer components into the surface of the metallic base. Limited diffusion bonding will not significantly change the material properties of the metallic base 23. Thus, the metallic base 23 can maintain its mechanical properties.

Tie layer 26 is bonded to at least a portion of the metallic base 23 and has an outer rough surface 27 to accommodate adhesion of first layer 28. The tie layer 26 includes magnesium or a magnesium-based alloy. As used herein, a magnesium-based alloy is an alloy having more magnesium by weight percentage than any other individual element. In some embodiments, a magnesium-based alloy includes at least 50 weight percent magnesium. In other embodiments, the magnesium-based alloy includes at least 75 weight percent magnesium. The magnesium or magnesium-based alloy is bioerodible. Accordingly, the magnesium degrades within a physiological environment when exposed to body fluids to yield the metallic base 23 as a bare metal stent.

The tie layer can have a thickness of between 1 micrometer and 20 micrometers. The tie layer 26 can be attached to the metallic base 23 via metallurgical bonding between the magnesium of the tie layer 26 and the metal of the metallic base 23 due to a limited diffusion exchange (limited alloying) between the magnesium and the elements of the metallic base 23 along an interface 25. The limited alloying can be controlled by depositing the magnesium or magnesium-based alloy tie layer onto the metallic base 23 without heating the metallic base 23 above its melting temperature. For example, magnesium has a melting temperature of about 650° C. while stainless steels can have a melting temperature of about 900° C. Moreover, magnesium has a very limited solubility in iron and iron-based alloys. Accordingly, when molten magnesium is applied to iron or an iron-based alloy, a limited but sufficient amount of magnesium diffuses into the iron or iron-based alloy, and a limited amount of iron diffuses into the liquid magnesium to fuse the magnesium to the iron or iron-based alloy. By having limited alloying between the magnesium and the metallic base 23, the surface properties of the metallic base 23 are not significantly changed. Accordingly, the tie layer 26 may erode and leave the exposed metallic base 23 with a stable and biocompatible surface. A more integral bond between a tie layer and a metallic base could result in a highly pitted and partially corroded surface of a metallic base after the bonded tie layer erodes, which could result in unwanted biological reactions such as an adverse immune response. Accordingly, a tie layer deposited at a temperature below the melting temperature of the metallic base 23 can permit the metallic base 23 to retain its structural and biocompatible properties.

The tie layer can have a cast microstructure including dendritic grains. The metallic base 23 has a wrought microstructure. Dendritic grains are not equiaxed like the grains of a wrought microstructure. Accordingly, the dendritic grains may protrude form the surface of the tie layer to create the roughened surface 27 of the tie layer 26. In some embodiments, at least 50 percent of the surface of the tie layer comprises dendritic grains. In some embodiments, the tie layer comprises at least 50 percent by volume of dendritic grains. In some embodiments, the grain structure can include a both equiaxed grains and dendritic grains. In some embodiments, the tie layer can include a concentration gradient of grains. For example, may have a greater concentration of dendritic grains along the outer surface to provide the rough outer surface. For example, a thin film of equiaxed grains can form where the magnesium first contacts the wrought substrate containing equiaxed grains. But as the solidification front moves from the first solid film that forms into the remaining molten metal, the grains may adapt a structure from the temperature gradient rather than the nucleation sites on the solid metal and result in the dendrite structure. The grain morphologies can be modified by heating the magnesium bath to different temperatures. At temperatures near the magnesium melting temperature, the liquid metal will very rapidly solidify and have more of an equiaxed structure. If the bath temperature is relatively high (e.g, greater than 750 C), the grains can form as columnar dendritic grains. In other embodiments, essentially all of the magnesium or magnesium-based alloy is in the form of dendritic grains. The dendritic grains may have a length (i.e., a maximum dimension) between 10 micrometers and 50 micrometers.

A cast microstructure can be formed by depositing the magnesium or magnesium-based alloy in a manner that minimizes the cooling rate. A slow cooling rate can be obtained by heating the metallic base 23 prior to or during the process of depositing molten magnesium and/or magnesium-based alloy. The metallic base 23 should be maintained below its melting temperature to limit the amount of diffusion with the magnesium and/or magnesium-based alloy. For example, a stainless steel metallic base 23 may be heated to a temperature of between 500° C. and 800° C. The source of heat can be removed prior to, during, or after the process of depositing the molten magnesium and/or magnesium-based alloy. In some embodiments, the source of heat is removed within 10 seconds of completing the magnesium deposition process. In another embodiment, the stent is fixtured upon a mandrel made of a material with low thermal conductivity, such as a ceramic. The stent substrate thereby cools slowly upon exiting from the coating batch. Other possible methods can include using a superheated coating batch, e.g., magnesium heated to above 750 C.

Figure 3:
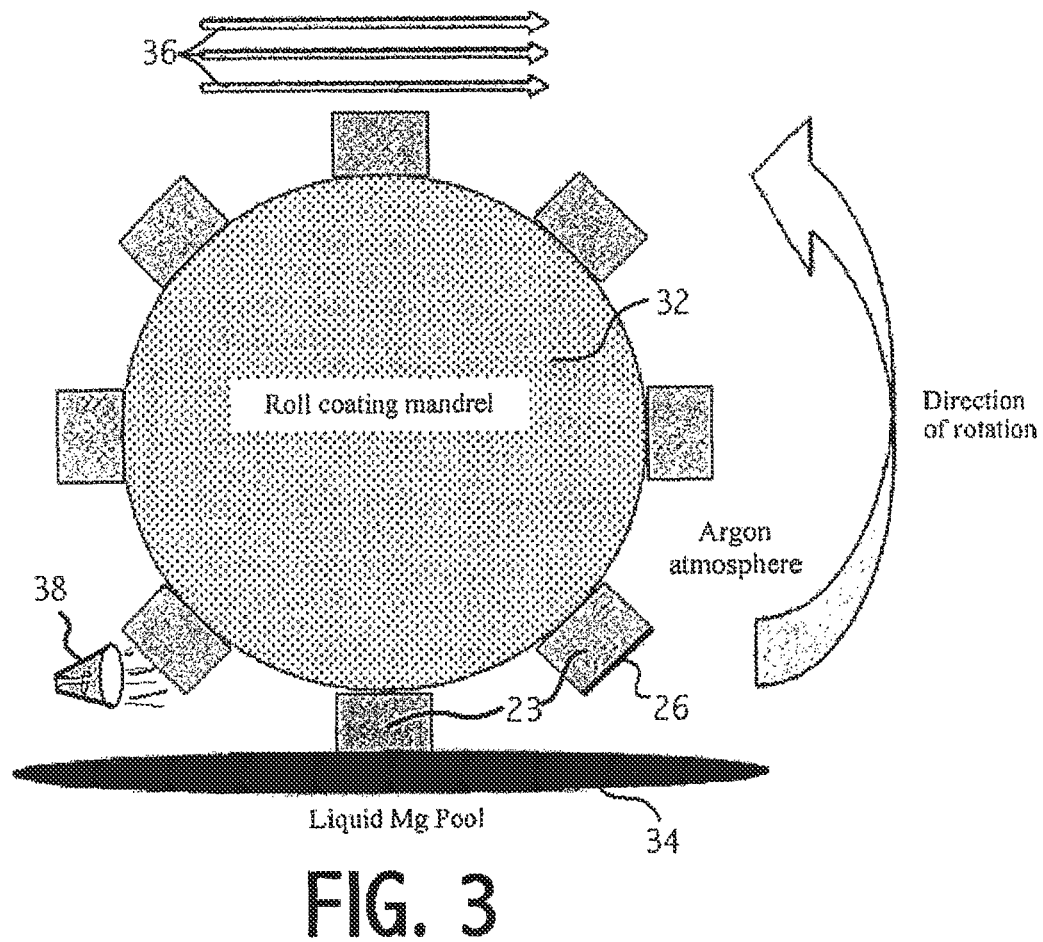
FIG. 3 illustrates an exemplary method for depositing the tie layer onto struts of a stent.

FIG. 3 depicts an exemplary apparatus for roll coating the tie layer 26 onto the abluminal surface of a metallic base 23 having a plurality of struts. The metallic base 23 is deposited over a roll first layer mandrel 32. The mandrel 32 is positioned such that an abluminal surface of at least one strut is positioned to contact a bath 34 of the molten magnesium and/or the molten magnesium-based alloy. The first layer process may occur in an inert gas atmosphere, which can keep the molten magnesium from combusting. For example, as shown in FIG. 3, an argon atmosphere may be used to avoid unwanted reactions between the magnesium and the metal(s) of the metallic base 23. An optional flow of inert gas 36 may also be used to control the cooling rate of the magnesium or the magnesium-based alloy. The temperature, flow rates, and flow pattern of the inert gas 36 can impact the cooling rate of the magnesium or the magnesium-based alloy. In some embodiments, the inert gas 36 may flow in a direction opposite to the direction of rotation. The mandrel 32 can, in some embodiments, apply heat to the metallic base 23. In some embodiments, heat may be applied to the stent via a quartz lamp 38.

The tie layer 26, in some embodiments, is porous. For example, a shrinkage porosity within the tie layer may be produced by quickly cooling of the tie layer 26. The cooling rate can be accelerated by having a room temperature or cooled the metallic base 23 and/or by using cooled inert gas during the deposition process. For example, a gas nozzle can be used to impinge argon gas on the coated surface immediately after it emerges from the coating bath. The argon gas can cool the surface by convection thereby increasing the cooling rate. Moreover, gas molecules can become entrapped in the solidifying metal creating gas porosity in addition to shrinkage porosity.

The tie layer 26 can also include particles within a matrix of the magnesium or the magnesium-based alloy. The particles can partially protrude from the surface of the tie layer to provide the roughened surface. Particles having a dimension greater than the thickness of other portions of the magnesium or magnesium-based alloy tie layer 26 can ensure that the particles partially protrude from the surface to create the roughened outer surface 27. The particles can have a maximum dimension of between 10 microns and 50 microns. The particles can be iron particles, calcium powder, graphite spheres, graphite nanotubes, barium powder, or a combination thereof. In some embodiments, the particles comprise a bioerodible iron or bioerodible iron alloy that may bioerode with the magnesium or the magnesium-based alloy.

A roughened surface on the tie layer may also be produced by using a turbulent flow of inert gas to cool the molten magnesium or magnesium-based alloy. In some embodiments, the cool gas is super cooled. The air flow of cool gas can be directed to create turbulent vortices that may generate waves or other topography in the molten magnesium or molten magnesium-based alloy. This process can be used either alone or in combination with the other processes discussed above. For example, the air flow of cool argon gas 36 of FIG. 3 can be used to create the waves or other topography. Heat can further be applied to the stent during the application of the magnesium and/or magnesium-based alloy to slow the cooling rate of the magnesium and thus increase the time for manipulating the topography of the molten magnesium or magnesium-based alloy before the tie layer solidifies. Heat can be applied in a number of manners. For example, heat may be applied to the stent via the mandrel 32 and/or by using a quartz lamp 38. Moreover, heating the metallic base 23 can reduce the cooling rate and thus also crease a cast microstructure.

The tie layer 26, in some embodiments, includes a magnesium-based alloy. In some embodiments, the magnesium-based alloy can include one or more metals having a melting temperature of less than 900° C. For example, zinc (420° C.), aluminum (660° C.), calcium (842° C.), tin (232° C.), and certain rare earth metals have melting temperatures of less than 900° C. Unlike pure metals, alloys melt over a range of temperatures. This melting temperature range can be used to produce the roughened surface of the tie layer. For example, melting a magnesium-based alloy within this range can result in a momentary combination of both liquids and solids as the material cools, thereby creating in multiple phases once the tie layer solidifies. Acid etching can be used as well to selectively dissolve one or more phases to create a microscopic roughened surface.

In some embodiments, the magnesium-based alloy can be made in situ after a layer of magnesium is bonded to the metallic base 23. For example, liquid tin can be applied to a first layer of magnesium at a temperature below the melting point of magnesium. Because tin has a lower melting point than magnesium, the tin can be applied without melting the magnesium. The layered structure could then be heated (e.g., with a quartz lamp 38) to a temperature or temperatures of between 200° C. and 650° C. For example, the layered structure could be heated in inert gas at a temperature of between 205-230 C for 1 hour. Initially there will be some solid state diffusion between the tin and magnesium. Then when there is sufficient tin in the magnesium, a eutectic reaction may occur between the tin and magnesium wherein the tin will melt, diffuse, and form a diffusion bond with the magnesium to form an alloy of magnesium and tin without having the tin and magnesium significantly alloy with the metallic base 23. The in situ formation of the magnesium-based alloy can result in a concentration gradient of different elements within the magnesium-based alloy of the tie layer. Once the alloy is formed, the cooling rate can be controlled to form the rough outer surface (e.g., to create dendritic grains or to create shrinkage-induced porosity).

The first layer 28 overlying the tie layer 26 can include a polymer, a ceramic, a metal, an organic substance, and/or a therapeutic agent. For example, ceramics such as titanium oxide, aluminum oxide, zinc oxide, silicon oxide, and iridium oxide can provide a pro-healing surface. The tie layer 26 can promote the adhesion of a preheating surface to the stent 20. In some embodiments, the stent 20 includes multiple layers deposited over the tie layer 26.

In some embodiments, the first layer 28 includes one or more therapeutic agents. The therapeutic agent can be alone, in a polymer matrix, in a organic matrix, or in a ceramic matrix. The therapeutic agent may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary bio-molecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, and smooth muscle cells.

Certain therapeutic agents can react with the magnesium or the magnesium-based alloy to accelerate the erosion of the tie layer and/or degrade the therapeutic agent. Accordingly, the therapeutic agent can be segregated from the tie layer. In some embodiments, the therapeutic agent is segregated from the tie layer with an essentially non-porous and conformal coating of a polymer, a ceramic, or an organic substance, whereby the therapeutic agent can be deposited over the non-porous and conformal coating. In some embodiments, the non-porous and conformal coating can include titanium oxide, aluminum oxide, zinc oxide, silicon oxide, and/or iridium oxide. A barrier layer disposed over the therapeutic agent can also be used for controlling the release of the therapeutic agent. The barrier layer can be a porous, inorganic layer deposited by atomic layer deposition. When the barrier layer is deposited over the therapeutic agent, the deposition temperature may be selected to avoid or reduce heat degradation of the therapeutic agent. For example, a deposition temperature of less than 125° C. may be useful for preserving the therapeutic agent during the deposition process. Deposition temperatures as low as 50° C. may be used for barrier layers such as aluminum oxide.

Stent 20 can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of about 2 mm to about 6 mm. In some embodiments, a peripheral stent can have an expanded diameter of about 4 mm to about 24 mm. In certain embodiments, a gastrointestinal and/or urology stent can have an expanded diameter of about 6 mm to about 30 mm. In some embodiments, a neurology stent can have an expanded diameter of about 1 mm to about 12 mm. An abdominal aortic aneurysm (AAA) stent and a thoracic aortic aneurysm (TAA) stent can have a diameter of about 20 mm to about 46 mm. The stent can be balloon-expandable, self-expandable, or a combination of both (e.g., see U.S. Pat. No. 6,290,721).

Stent 20 can also be part of a covered stent, a stent-graft and/or other endoprostheses.

Figure 4:
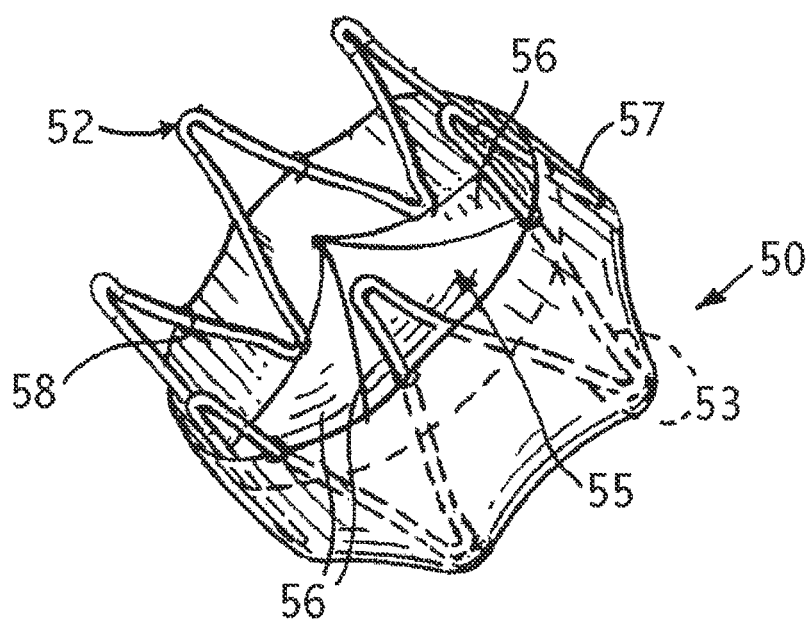
FIG. 4 is a perspective view of an artificial heart valve in an expanded configuration.

The endoprosthesis, in some embodiments, can be an artificial heart valve. For example, an artificial heart valve 50 is depicted in FIG. 4. The heart valve 50 has a generally circular shape. A stent member 52 is formed of a wire including a metallic base, a tie layer, and optionally a first layer. The stent member 52 is formed in a closed, zig-zag configuration. In other embodiments, the stent member of the artificial heart valve can include a plurality of bands with connectors in between. The valve member 55 is flexible and includes a plurality of leaflets 56. The leaflet portion of the valve member 55 extends across or transverse of the cylindrical stent member 52. The leaflets 56 are the actual valve and allow for one-way flow of blood. Extending from the periphery of the leaflet portion is a cuff portion 57. The cuff portion is attached to the stent by sutures 58. Sutures 53 can be used to attach the artificial heart valve 50 to heart tissue. The valve member 55 can be formed of polymer such as polytetrafluoroethylene or a polyester. In other embodiments, the valve member 55 can be a bioerodible polymer. In some embodiments, the valve member 55 can be adhered to the tie layer direct.

The tie layer 26 may also be applied to metallic bases of other types of medical implants. For example, orthopedic implants, bioscaffolding, bone screws, and aneurysm coils may all have one or more of the tie layers described herein.

All publications, patent applications, patents, and other references mentioned herein are incorporated by reference herein in their entirety.

A number of embodiments have been described. Nevertheless, it will be understood that various modifications may be made without departing from the spirit and scope of this disclosure. Accordingly, other embodiments are within the scope of the following claims.

What is claimed is:

1. A medical implant comprising:
a metallic base;
a tie layer bonded to at least a portion of a surface of the metallic base, the tie layer comprising magnesium or a magnesium-based alloy, the tie layer having an outer surface comprising dendritic grains, the tie layer comprising at least 50 weight percent magnesium; and
at least a first layer overlying the outer surface of the tie layer.

2. The medical implant of claim 1, wherein the first layer comprises at least one therapeutic agent.

3. The medical implant of claim 1, wherein the first layer comprises a polymer.

4. The medical implant of claim 1, wherein the metallic base comprises a biostable metal.

5. The medical implant of claim 1, wherein the metallic base comprises a metal selected from the group consisting of stainless-steels, platinum-enhanced stainless steels, cobalt-chromium alloys, nickel-titanium alloys, niobium-based alloys, titanium-based alloys, and tantalum-based alloys.

6. The medical implant of claim 1, wherein the metallic base comprises a bioerodible metal.

7. The medical implant of claim 1, wherein the metallic base comprises a metal having a melting temperature greater than the melting temperature of the magnesium or the magnesium-based alloy of the tie layer.

8. The medical implant of claim 1, wherein the metallic base comprises a metal having a melting temperature of 700° C. or greater.

9. The medical implant of claim 1, wherein the tie layer has an average thickness of between 1 micrometer and 20 micrometers.

10. The medical implant of claim 9, wherein the first layer comprises at least one therapeutic agent, a polymer, or a combination thereof.

11. The medical implant of claim 9, wherein the metallic base comprises a metal selected from the group consisting of stainless-steels, platinum-enhanced stainless steels, cobalt-chromium alloys, nickel-titanium alloys, niobium-based alloys, titanium-based alloys, and tantalum-based alloys, wherein the metallic base has a melting temperature greater than the melting temperature of the tie layer.

12. The medical implant of claim 9, wherein the dendritic grains have a maximum dimension of between 10 microns and 50 microns.

13. The medical implant of claim 1, wherein the dendritic grains have a maximum dimension of between 10 microns and 50 microns.

14. The medical implant of claim 1, wherein the tie layer further comprises particles within a matrix of the magnesium or the magnesium-based alloy, wherein the particles partially protrude from the surface of the tie layer to provide a rough surface, the particles comprising a maximum dimension of between 10 microns and 50 microns.

15. The medical implant of claim 14, wherein the particles are selected from the group consisting of iron particles, calcium powder, graphite spheres, graphite nanotubes, barium powder, and combinations thereof.

16. The medical implant of claim 1, wherein the tie layer comprises an alloy of magnesium with one or more elements selected from the group consisting of zinc, aluminum, calcium, tin, and rare earth metals.

17. The medical implant of claim 1, wherein the medical implant is a stent; the metallic base comprising a plurality of bands and a plurality of connectors extending between adjacent bands; and the surface of the metallic base is at least a portion of an abluminal surface of the bands and connectors.

18. A medical implant comprising:
a metallic base;
a tie layer bonded to at least a portion of a surface of the metallic base, the tie layer
(a) comprising magnesium or a magnesium-based alloy;
(b) having an average thickness of between 1 micrometer and 20 micrometers; and (c) having a rough outer surface defined by pores, projecting grain structures, projecting particles at least partially embedded in the magnesium or the magnesium-based alloy, or a combination thereof; and at least a first layer overlying the rough outer surface of the tie layer.

19. The medical implant of claim 18, wherein the tie layer comprises at least 50 weight percent magnesium.

\* \* \* \* \*